United States Patent [19]

Zall et al.

[11] Patent Number: 4,900,670

[45] Date of Patent: Feb. 13, 1990

[54] MICROBIOLOGICAL PRODUCTION OF ACETALDEYDE

[75] Inventors: Robert R. Zall, Ithaca, N.Y.; Matthew Wecker, Bellevue, Wash.

[73] Assignee: Cornell Research Foundation, Inc., Ithaca, N.Y.

[21] Appl. No.: 159,153

[22] Filed: Feb. 23, 1988

[51] Int. Cl.$^4$ ............................ C12R 1/01; C12P 7/24
[52] U.S. Cl. ................................. 435/147; 435/252.1; 435/822
[58] Field of Search ...................... 435/147, 252.1, 822

[56] References Cited

U.S. PATENT DOCUMENTS

| | | |
|---|---|---|
| 4,347,109 | 8/1982 | Meshbesher et al. . |
| 4,481,292 | 11/1984 | Raymond et al. . |
| 4,742,006 | 5/1988 | Bringer et al. ................... 435/822 |
| 4,816,399 | 3/1989 | Lawford ............................ 435/822 |

FOREIGN PATENT DOCUMENTS

| | | |
|---|---|---|
| 1092580 | 5/1986 | Japan ................................. 435/147 |
| 2079280 | 1/1982 | United Kingdom ................ 435/147 |

OTHER PUBLICATIONS

Bringer et al, 1984, *Arch. Microbiol.,* 139:376–381.
Wills et al, 1981, *Arch. Biochem. Biophy.,* 210:775–780.
Wills et al, 1979, *Eur. J. Biochem.,* 99:323–331.
Barrow et al, 1984, *Appl. Microbiol. Biotechno.,* 20:225–232.
Viikari, 1984, *Appl. Microbiol. Biotechnol.,* 20:118–123.
Kalter et al, 1981, ERDA Report #81-7, pp. 136–144.
Byrne et al, 1984, *Food Technology,* 38:57–61.
Kierstan, 1982, *Biotech. Bioeng.,* 24:2275–2277.
Armstrong et al, 1984, *Biotech. Lett.,* 6:183–188.
Trevino,. 1985, USDOE File #DE85016220.
Jones et al, 1986, *J. Food Sci.,* 51:229–230.

*Primary Examiner*—Herbert J. Lilling
*Attorney, Agent, or Firm*—Jones, Tullar & Cooper

[57] ABSTRACT

Acetaldehyde producing strains of *Zymononas mobilis* are produced by selection against allyl alcohol. The selected strain produces acetaldehyde in a carbohydrate containing medium under direct aeration.

5 Claims, 5 Drawing Sheets

MICROBIOLOGICAL PRODUCTION OF ACETALDEYDE

BACKGROUND OF THE INVENTION

In the fermentation of ethanol, the ultimate step in the pathway is the reduction of acetaldehyde to ethanol by the enzyme alcohol dehydrogenase. The product ethanol must then be separated from the reaction mixture, an energy-intensive process which may account for 63% of the total energy use involved in the fermentation process [Kalter et al (1981) ERDA report #81-7 pp. 136-144]. If the reaction pathway is altered, however, to inhibit the reduction of acetaldehyde to ethanol, the acetaldehyde produced might be collected as an attractive alternative to ethanol.

Pure acetaldehyde has a boiling point of 20.8° C., whereas ethanol boils at 78.5° C. Thus, at temperatures typical for mesophilic fermentation, acetaldehyde may be more readily stripped from solution than ethanol. In addition to the advantage of having greater volatility than ethanol, acetaldehyde does not form an azeotrope with water. In January, 1987, 99% acetaldehyde had a market place value nearly 1½ times that of synthetic 100% ethanol and a value approximately twice that of fermentation ethanol. Acetaldehyde is quite reactive and can be used to produce a variety of compounds such as acetic acid, acetic anhydride, ethyl acetate, butanol, and pyridines. Acetaldehyde also has uses in the food industry as a flavor additive. It is listed as a GRAS (Generally Recognized As Safe) substance by the U.S. Food and Drug Administration and delivers a "fresh" and/or "fruity" flavor to foods such as meats, fruits, breads, spices, vegetables, and dairy products, as well as to candies and chewing gums. Since acetaldehyde is both volatile and reactive, dry acetaldehyde delivery systems are currently being developed for use in dry flavors and instantized foods [Byrne et al (1984) *Food Technology* 38:57–61].

Previous research on the commercial production of acetaldehyde by biological means has been limited to the reoxidation of biologically produced ethanol back to acetaldehyde. Kierstan (1982)*Biotech. Bioeno.* 24:2275–2277, conducted a preliminary study on the feasibility of using a free enzyme system to oxidize aqueous solutions of ethanol to acetaldehyde. This enzyme system consisted of the alcohol oxidase from *Candida boidinii* and a catalase. Similarly, U.S. Pat. No. 4,481,292 was issued for the production of acetaldehyde from ethanol using an enzyme complex containing alcohol dehydrogenase, NADH, flavine mononucleotide, and a catalase. Using this system, a conversion of 10–20% of the ethanol was obtained; after nine hours, acetaldehyde was produced at a level of 2.5 g/l of solution. Armaldehyde strong et al, (1984) *Biotech. Lett.* 6:183–188 have researched the use of whole cells of *Candida utilis* for the conversion of ethanol to acetaldehyde. The maximum accumulation of acetaldehyde occurred at a level of 6.5% ethanol in solution, with 3.5 g/l acetaldehyde accumulating in batch culture after 5 hours of growth. No increase in acetaldehyde was noted upon additional incubation. Production of acetaldehyde by this method, however, must be carefully regulated so as to limit the conversion of acetaldehyde to acetic acid. The Electrohol process developed by Meshbesher (U.S. Pat. No. 4,347,09) electrochemically converts fermentation alcohol to acetaldehyde. In an assessment of the process, Trevino (1985) USDOE File #DE85016220, determined that yields of 93% or greater must be obtained in order for it to be competitive with the current ethyene-based technology of acetaldehyde manufacture. The Electrohol process is most efficient with a feed stream of 95% ethanol. As the ethanol concentration in the feed stream is reduced, the efficiency of this process drops considerably.

*Zymomonas. mobilis* is known to produce acetaldehyde in the presence of oxygen [Schreder et al (1934) *Biochem Z.* 273:223–242]. This is due to increased NADH oxidase activity resulting in the decreased availability of NADH for the reduction of acetaldehyde to ethanol by alcohol dehydrogenase. In addition, *Z. mobilis* apparently does not have an aldehyde dehydrogenase to oxidize acetaldehyde to acetic acid (Bringer et al, 1984, *Arch. Microbiol.* 139:376–381). Alcohol dehydrogenase mutants of *Z. mobilis* showing increased levels of acetaldehyde production have previously been isolated using allyl alcohol as a selective agent Wills et al 1981, *Arch. Bioch. Biophy.* 210:775–780. FIG. 1 depicts the effects of oxygen and allyl alcohol upon glucose metabolism in *Z. mobilis*.

The general principles of the fermentation are including growth kinetics, the isolation, preservation and improvement of microorganism, media requirements, sterilization, development of inocula fermente design and control, aeration and agitation and the like are well known; see for example "Principles of Fermentation Technology", by Stanbury and Whitaker, Pergamon Press, 1984. Likewise, the growth characteristics, medium requirements and the like of *Zymononas mobilis* are well known.

DESCRIPTION OF THE INVENTION

Figure 1:
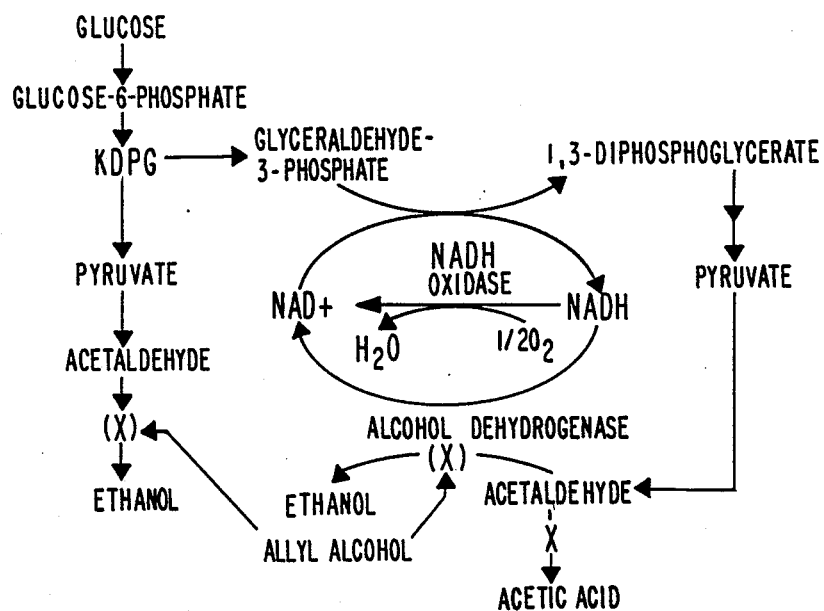
FIG. 1 shows the Entner-Duoderoff pathway for glucose metabolism in *Zymomonas mobilis;* the effects of oxygen and allyl alcohol.

This invention comprises forming and selecting alcohol dehydrogenase negative strains of *Zymomonas mobilis*, and further selecting therefrom a strain which produces increased levels of acetaldehyde, especially when employed in an aeration process. It is noted that the so called "dehydrogenase negative" strains described herein are not completely devoid of activity, but have very markedly diminished activity.

The alcohol dehydrogenase negative strain of *Z. mobilis* is selected by cultivating a *Z. mobilis* strain sensitive to allyl alcohol, in the presence an amount of allyl alcohol and for a time less than sufficient to kill the entire *Z. mobilis* population, but sufficient to kill a majority of the population (preferably in excess of 99%, for example a survivorship of 1 in $51 \times 10^8$). The remaining *Z. mobilis* population or a portion thereof is isolated and recultured in the presence of an increased amount of the allyl alcohol, again an amount and a time less than sufficient to kill the entire *Z. mobilis* population, but sufficient to kill a majority of the population. This procedure is repeated for sufficient passages with increasing amounts of allyl alcohol to provide a *Z. mobilis* strain with diminished or absent alcohol dehydrogenase activity and therefor potentially increased acetaldehyde production.

The resultant allyl alcohol selected *Z. mobilis* strain is then screened to select a strain therefrom which produces increased levels of acetaldehyde, for example by a plate test which indirected levels of acetaldehyde production, for example, the acid fuchsin overlay test described hereinafter, and/or by selection based on culturing the strain in a acetaldehyde producing growth medium and measuring acetaldehyde production.

The starting allyl alcohol selected strain for the above further-selected acetaldehyde producing strain preferably is then subjected to a combined chemical mutation/acetaldehyde tolerance process wherein the strain is subjected to chemical mutation using a mutagen, such as for example, nitrosoguanidine, followed by selection by culturing in the presence of vapor phase acetaldehyde.

The chemical mutation process is not indirectly critical and it is believed that any of the mutation processes known in the art can be utilized. The *Z. mobilis* population surviving mutagenisis is then grown in the presence of a predetermined level of acetaldehyde thereby selecting an acetaldehyde tolerant strain of *Z. mobilis*.

In the acetaldehyde production process of the invention an acetaldehyde producing strain of *Z. mobilis* as selected above, is employed in a direct aeration production using a sugar based (e.g. sucrose or glucose, preferably glucose) growth medium in a manner such that sufficient oxygen is flowing through the system so as to substantially completely remove acetaldehyde from the growth medium as it is formed; thereby reducing acetaldehyde inhibition of the system. In addition, it is believed that that amount of oxygen also favorably affects the enzyme activity to cause acetaldehyde production.

While oxygen is preferred, air or other non-toxic oxygen containing gas mixture can be employed.

The aerobic fermentation process of the invention either as a batch or as a continuous process is typically conducted between about 25° and about 30° C., although higher temperature up to about 37° C. could be employed. The medium, in addition to sugar, should contain a source of biotin and pantothenate and salts. Presently preferred media are described in the examples.

The aeration stream after passing through the medium is subjected to product recovery to capture the product acetaldehyde. Procedures standard in the art to recover acetaldehyde from a gas stream can be improved, including physical means such as cold condensers and/or solvent baths (with or without subsequent further distillation to enhance purity), and/or chemical means such as passing the gas through a bisulfite solution to form an aldehyde-bisulfite addition product which can be subsequently disassociated with a base to recover the acetaldehyde.

EXAMPLE

Mutants of *Zymomonas mobilis* were selected for decreased alcohol dehydrogenase activity using consecutively higher concentrations of allyl alcohol. A mutant selected using 100 mM allyl alcohol produced acetaldehyde at a level of 4.08 g/l when grown in aerated batch culture on a medium containing 4.0% (wt/wt) glucose. Based upon the amount of glucose utilized, this level of acetaldehyde production represents nearly 40% of the maximum theoretical yield. Acetaldehyde produced during growth was continuously air-stripped from the reactor. Acetaldehyde present in the exhaust stream was then trapped as the acetaldehyde-bisulfite addition product in an aqueous solution of sodium bisulfite and released by treatment with base. Acetaldehyde was found to inhibit growth of *Z. mobilis* at concentrations as low as 0.05% (wt/wt) acetaldehyde. An acetaldehyde tolerant mutant of *Z. mobilis* was isolated following both mutagenesis with nitrosoguanidine and selection in the presence of vapor phase acetaldehyde.

MATERIALS AND METHODS

Strain and cultivation

The organism used in this study was *Z. mobilis* subs. mobilis (ATCC 10988). Cultures were maintained by culturing in either 4% glucose standard medium (4GSM) or 4% sucrose standard medium (4SSM). The components of the standard medium were (g/100 ml distilled $H_2O$) sucrose or glucose, 4.0; Bacto Peptone (Difco, Detroit, Mich., USA), 2.0; Bacto Yeast extract, 1.0; $KH_2PO_4$, 0.1; $(NH_4)_2SO_4$, 0.1; and $MgSO_4.7H_2O$, 0.05. For solidification, Bacto agar was added at 1.5 g/100 ml unless otherwise indicated. The pH was adjusted to 5.5 prior to steam sterilization at 121° C. and 15 p.s.i. for 15 minutes. Cultures were maintained in screw cap tubes by transferring every two days using 1.0% inocula. All cultures were incubated aerobically at 30° C. in order to select for those organisms most suited to function under aerobic conditions. Since the prolonged growth of *Z. mobilis* upon sucrose results in the loss of the Zymomonas 110 acetaldehyde dehydrogenase II enzyme [Wills et al (1981) Arch. Bioch. Biophy. 210:775-780], the wild type was maintained in both 4GSM and 4SSM.

Analytical methods

Acetaldehyde and ethanol concentrations in cell cultures were measured using a Varian 6000 gas chromatograph (Varian Instrument group, Walnut Creek, Calif., USA) fitted with a flame ionization detector. A Varian 4290 integrator was used for peak integration. A one meter column was used with Porapak Q-S 80/100 mesh as the packing material. The following gas chromatograph settings were used: carrier nitrogen, 30 ml/min; air, 300 ml/min; hydrogen, 30 ml/min; column, 150° C.; injector, 180° C.; detector, 190° C. Culture samples were centrifuged for ten minutes at 4° C. and 3000 rpm prior to analysis. Isopropanol was added at a level of 0.1% (wt/wt) to each sample as an internal standard. An external standard of 0.1% (wt/wt) acetaldehyde (Fisher Scientific, Co., Fairlawn, N.J., USA), 0.1% (wt/wt) ethanol, and 0.1% (wt/wt) isopropanol was prepared daily. All solutions to which acetaldehyde was added were cooled to approximately 0° C. prior to addition. Glucose concentration was determined enzymatically using the Sigma Glucose (HK)10 single reagent system (Sigma Chemical Co., St. Louis, Mo., USA). All analyses were done in triplicate.

Differentiation of strains with the use of acid fuchsin

The amount of acetaldehyde produced by plate cultures was qualitatively assessed at 76 hours of growth using a 0.5 cm ajar overlay containing acid fuchsin (Sigma Chemical Co.) as an indicator. The overlay medium was buffered to pH 5.5 to limit the false-positive reaction of acid fuchsin with acid production by the colonies. The overlay medium consisted of the following (g/100 ml distilled $H_2O$): acid fuchsin, 0.02; $KH_2PO_4$, 3.18; $Na_2HPO_4.7H_2O$, 0.88; and agar, 2.0. Molten acid fuchsin medium at 45° C. was decolorized with $SO_2$ prior to use as an overlay. To increase the resolution of acetaldehyde production by colonies, the inoculum was diluted to limit the plate count to approximately 30 colonies. Diffusion of the acetaldehyde was limited by cooling the plates to 4° C. prior to applying the overlay and by developing the plates at 15° C.

Selection of strains by allyl alcohol

Allyl alcohol (Aldrich Chemical Co., Inc., Milwaukee, Wisc., USA) was used to select for those microorganisms with altered alcohol dehydrogenase activity. The initial level of allyl alcohol used was 0.2 mM (13.6 μl/l) as given by Wills et al, supra. A three-day-old, sucrose-grown, 25 wild type culture at $2.4 \times 10^9$ cells/ml was inoculated onto each of ten 4SSM 0.2 mM allyl alcohol plates without dilution. Twenty-eight strains were isolated from these plates and screened for acetaldehyde production using acid fuchsin overlays. Seven strains representing the entire range of color reaction to acid fuchsin were then grown on 2% Glucose Standard Medium (2GSM) in shake flask culture in order to compare levels of acetaldehyde production. The strain which showed both the strongest acid fuchsin reaction and the highest level of acetaldehyde production was then selected on media at consecutively higher concentrations of allyl alcohol: 2.0 mM (ten times the original level of allyl alcohol used: 10×), 10.0 mM (50×), 20.0 mM (100×) and 100.0 mM (500×). Selection of mutants on 4SSM with allyl alcohol was carried out over a period of six months.

Acetaldehyde production using shake flasks

Each culture used for shake culturing was transferred every 24 hours for three consecutive days prior to the final inoculation. Each transfer was made with a 1.0% inoculum into 125 ml, cotton-plugged Erlenmeyer flasks containing 50 ml of either 2GSM or 4GSM. Cultures were incubated in a waterbath shaker at 100 rpm. All trials were carried out in triplicate.

Acetaldehyde production with direct aeration

Figure 2:
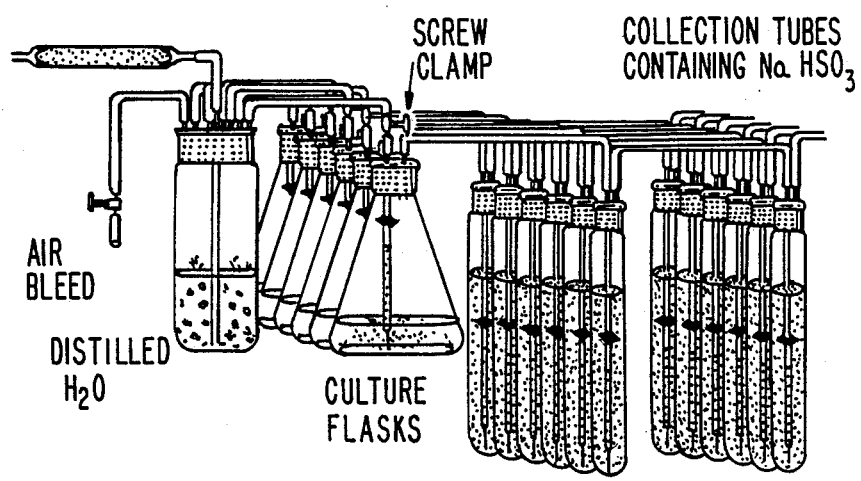
FIG. 2 schematically shows apparatus for aeration of *Zymomonas mobilis* cultures and collection of acetaldehyde from the exhaust stream.

Cultures were transferred every 24 hours for three days prior to the final inoculation. The final transfers were made using a 1% inoculum into 50 ml of 4GSM in 125 ml Erlenmeyer flasks. The flasks were allowed to incubate for 6 hours prior to direct aeration. Cultures were aerated at either 23 ml/min or at 11 ml/min. All trials were done in triplicate. Filtered air was distributed to each culture flask and released through syringes fitted with 26 gauge needles. Acetaldehyde was collected from the exhaust gas of each aerated culture flask by sparging the exhaust stream through two consecutive 25×200 mm screw cap tubes, each of which contained 50 ml of 0.25M $NaHS_3$ (see FIG. 2). The total yield of acetaldehyde from each flask was computed as the sum of the concentrations of acetaldehyde from the two collection tubes plus any residual concentration of acetaldehyde remaining in the culture medium. Acetaldehyde concentrations were corrected for any loss in fluid volume in the flasks or tubes due to aeration.

Quantification of acetaldehyde as present in solutions of $NaHSO_3$

Quantification of acetaldehyde trapped in solutions of $NaHSO_3$ was made using a modification of the method of Jones et al (986) *J. Food Sci.* 51:229-230. $NaHSO_3$ solutions were diluted to 0.05M prior to analysis. All chemistry was carried out at room temperature under constant stirring. One milliliter of 20% HCl was added to 10 ml of the $NaHSO_3$ solution and allowed to react for one minute. At this time, 2 ml of a $Na_3BO_3$ solution (10 g of $H_3BO_3$ and 17 g of NaOH to 100 ml $H_2O$) was added and titrated with a $KI-I_2$ solution (49.8 g of KI and 24.9 g of $I_2$ to 100 ml of $H_2O$) to give a lasting yellow color. The mixture was then brought to pH 9.00. After 5 minutes 20% HCl was added to bring the pH of the mixture to 7.00. This mixture was immediately transferred to a tared 100 ml serum bottle, isopropanol was added to 0.1% by weight, and the bottles were capped. Standards were made by adding 0.1% or 0.5% (wt/wt) acetaldehyde to the original strength $NaHSO_3$ solution. These standards were allowed to equilibrate while the other $NaHSO_3$ solutions were sparged with gas from the aerated cultures. The standards were then chemically treated in a manner identical to that of the test samples. All samples were allowed to equilibrate at 30° C. prior to determination of acetaldehyde concentration by gas chromatography. Gas chromatography was conducted under conditions identical to those given for the determination of acetaldehyde in solution, although injections were made with 0.5 ml of the headspace gas. All gas chromatograph sampling was done in triplicate.

Vapor phase selection for acetaldehyde tolerant mutants

Strains of *Z. mobilis* were selected for tolerance to acetaldehyde by growing the cultures in the presence of a mutagen under an atmosphere containing acetaldehyde. 4GSM agar plates were plated with a $1 \times 10^{-4}$ dilution of cells and incubated for a period of 3.5 hours prior to the addition of the mutagen N-methyl-N'-nitro-N-Nitrosoguanidine (NTG; Sigma Chemical Co.). The NTG was applied to the center of each plate using a 5 μl aliquot of a 5 mg/ml solution of NTG in 0.1M sodium citrate buffer. This level of NTG resulted in a 4–5 cm diameter of kill. The NTG-treated plates were then allowed to incubate for an additional 8.5 hours before being subjected to acetaldehyde vapor within GasPak System 100 chambers (BBL Microbiology Systems, Cockeysville, Md., USA). The chambers were supported horizontally and supplied with support racks for the petri plates. No catalyst was used with the chambers. A glass petri dish was placed at the bottom of each chamber and filled with 10 ml of a solution of given acetaldehyde concentration. A range of between 0.0% and 10.0% (wt/wt) acetaldehyde was used within the chambers. The plates were incubated in the GasPak chambers for 48 hours and then removed and incubated aerobically for 76 hours. Colonies were selected both on the basis of size and for growth near the approximate periphery of NTG kill.

Evaluating tolerance of strains to acetaldehyde

Mother cultures of 50 ml 4GSM in 125 ml Erlenmeyer flasks were transferred with a 1% inoculum every 24 hours for 3 days prior to the start of the experiment. Size 16×150 mm screw cap tubes containing 8.9 ml of 4GSM were used for growth analysis at various concentrations of acetaldehyde. Each tube was brought to 10.0 ml using transfers of sterile $H_2O$, acetaldehyde, and 0.1 ml inoculum. All trials were done in triplicate. All incubations were carried out in a waterbath shaker at 100 rpm. A Bausch and Lomb Spectronic 710 at 550 nm was used for the absorption studies in growth curve analysis. The percent of acetaldehyde in solution was measured both before and after growth in order to check for any change in acetaldehyde concentration due to growth. Tubes of media containing acetaldehyde at the given levels were left uninoculated as controls and were incubated at both 4° C. an 30° C. for the duration of the experiment.

RESULTS

Selection and differentiation of strains having increased acetaldehyde production After five days of aerobic growth on 0.2 mM allyl alcohol agar plates, twenty-eight colonies of Zymomonas mobilis subs. mobilis were obtained at a survivorship of approximately 1 in $1\times10^8$ cells. After ten days of growth the survivorship increased to about 1 in $1\times10^5$ cells. When clones of the twenty-eight strains were overlayed with decolorized acid fuchsin agar; the degree of reaction by the colonies corresponded to the level of acetaldehyde produced during shake flask culture using 2GSM. The range of acetaldehyde production from these shake flask trials was from 0.02% (wt/wt) acetaldehyde by the wild type to 0.08% (wt/wt) acetaldehyde by strain number 17. When strain 17 was selected using consecutively higher concentrations of allyl alcohol, there was an overall increase in acetaldehyde production and a decrease in ethanol production (See Table 1).

TABLE 1

Acetaldehyde and ethanol production by allyl alcohol mutants of Zymomonas mobilis. 4GSM shake flask culture without direct aeration

| Strain | Concentration of allyl alcohol used for strain (mM) | % Acetaldehyde produced | % Ethanol produced |
|---|---|---|---|
| Wild type | 0.0 | 0.078 | 1.32 |
| 17x | 0.2 | 0.071 | 1.38 |
| 17-10x | 2.0 | 0.087 | 1.37 |
| 17-50x | 10.0 | 0.139 | 1.11 |
| 17-500x | 100.0 | 0.248 | 0.14 |

Figure 3:
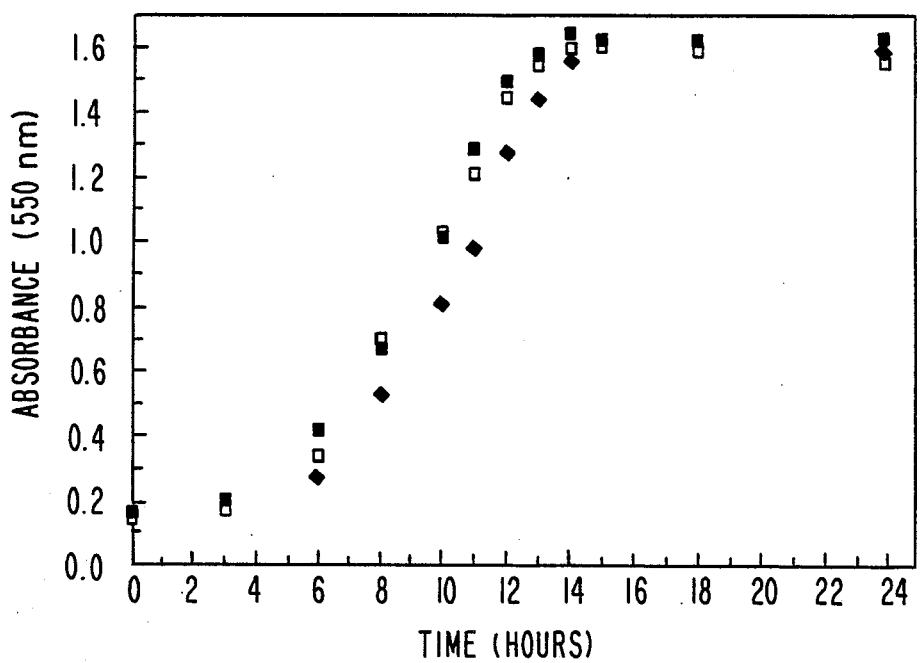
FIG. 3 shows growth curves of wild type and allyl alcohol selected strains of *Z. mobilis*. Symbols: ☐ wild type; ◆ strain 17; ■ 17-500x. Screw cap tube culture, 4GSM.
Figure 4:
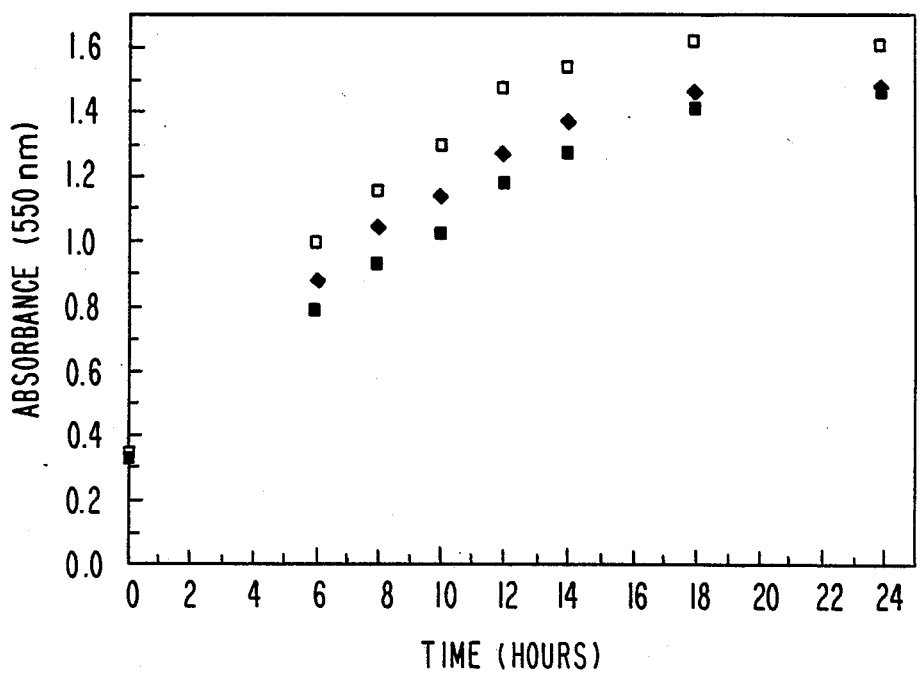
FIG. 4 shows growth curves of wild type and allyl alcohol selected strains of *Z mobilis.* Symbols: ☐ wild type; ◆ strain 17; ■ strain 17-500x. Shake flask culture, 4GSM.

The combined yield of acetaldehyde and ethanol, however, decreased for those strains selected using higher levels of allyl alcohol. This is in part related to a decrease in the amount of glucose utilized; the wild type and 17-500x strains grown in shake flask culture used respectively 97% and 52% of the available glucose. When the wild type and allyl alcohol selected strains were grown in screw cap tubes, the growth curves for the wild type and selected strains were quite similar (see FIG. 3). When these same strains were grown in shake flask culture, however, a decrease in growth rate was observed for those strains selected using allyl alcohol (see FIG. 4). After 41 days of subculturing, strain 17-500x showed a 38% decrease in acetaldehyde production when grown in 4GSM shake flask culture without direct aeration.

Acetaldehyde production using direct aeration

The level of acetaldehyde in solution decreased nearly exponentially with time when 50 ml to a 0.3% (wt/wt) solution of acetaldehyde in 4GSM was sparged with 250 ml/min of air (data not shown). Therefore, acetaldehyde may be readily stripped from the growth medium during culturing. When air is used to strip acetaldehyde from the culture medium, oxygen is delivered to the growing cells and acetaldehyde production by Z. mobilis increases. Table 2 shows the amount of acetaldehyde produced by both the wild type strain and strain 17-500x when the cultures are grown with 23 ml/min direct aeration. The allyl alcohol selected strain produced nearly twice as much acetaldehyde as that of the wild type. The amount of glucose utilized by strain 17-500x when grown under direct aeration, however, was only approximately 60% of that used by the wild type strain when the cultures were grown under direct aeration. Based on the amount of glucose utilized, strain 17-50x produced nearly 40% of the theoretical yield of acetaldehyde; three ties that of the wild type (see Table 2). In a comparison of data from Tables 1 and 2, there was an approximate twofold increase in acetaldehyde production when strain 17-500x was grown in the presence of direct aeration as opposed to shake flask culturing without direct aeration. When the flow of air was decreased to 11 ml/min, strain 17-500x produced only 2.1 g/l acetaldehyde. With either flow rate, the amount of acetaldehyde remaining in the medium after 24 hours was at a level of 0.11% (wt/wt).

The acetaldehyde levels shown in Table 2 are a total of that stripped from the medium and that remaining in the medium after 24 hours of growth. The method used for trapping the stripped acetaldehyde was approximately 79% efficient. Any loss of acetaldehyde due to this method of collection was not accounted for in the data of Table 2.

TABLE 2

Acetaldehyde production by directly aerated cultures of the wild type strain and 17-500x strain of *Z. mobilis*. 50 ml 4GSM in 125 ml Erlenmeyer flasks, 23 ml/min aeration, 24 hours

| Strain | Acetaldehyde production (g/l). | Glucose used (g/l) | % Theoretical yield of acetaldehyde |
|---|---|---|---|
| Wild type | 2.20 | 34.5 | 13.0 |
| 17-500x | 4.08 | 21.0 | 39.7 |

Vapor phase selection for acetaldehyde tolerant mutants

Figure 5:
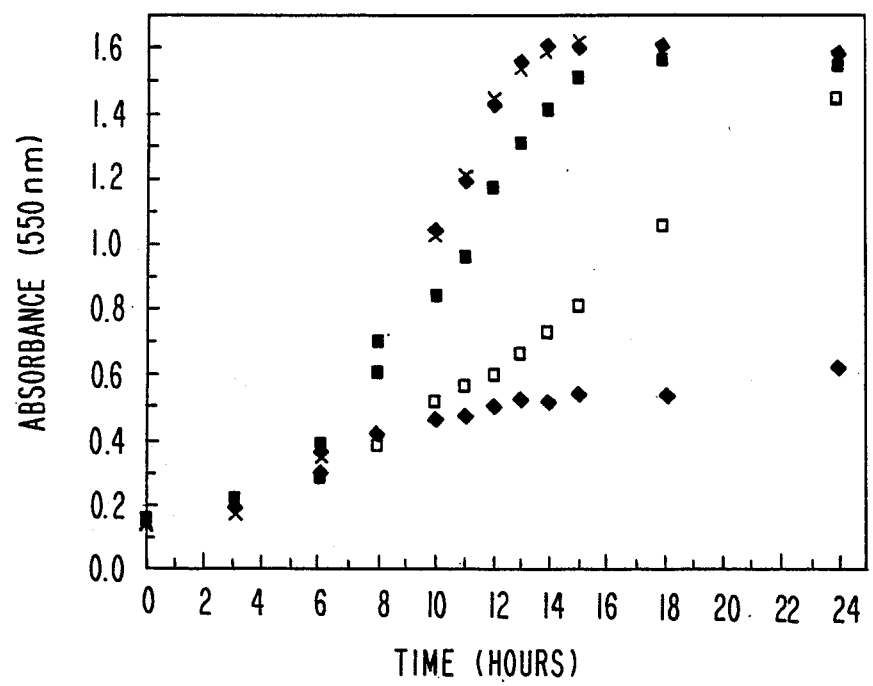
FIG. 5 graphically shows growth inhibition of wild type *Z. mobilis* by acetaldehyde. Symbols: x 0.0% (w/w) acetaldehyde; ◆ 0.01%; ■ 0.05%; ☐ 0.1%; ◆ 0.2%. Screw cap tube culture, 4GSM.
Figure 6A:
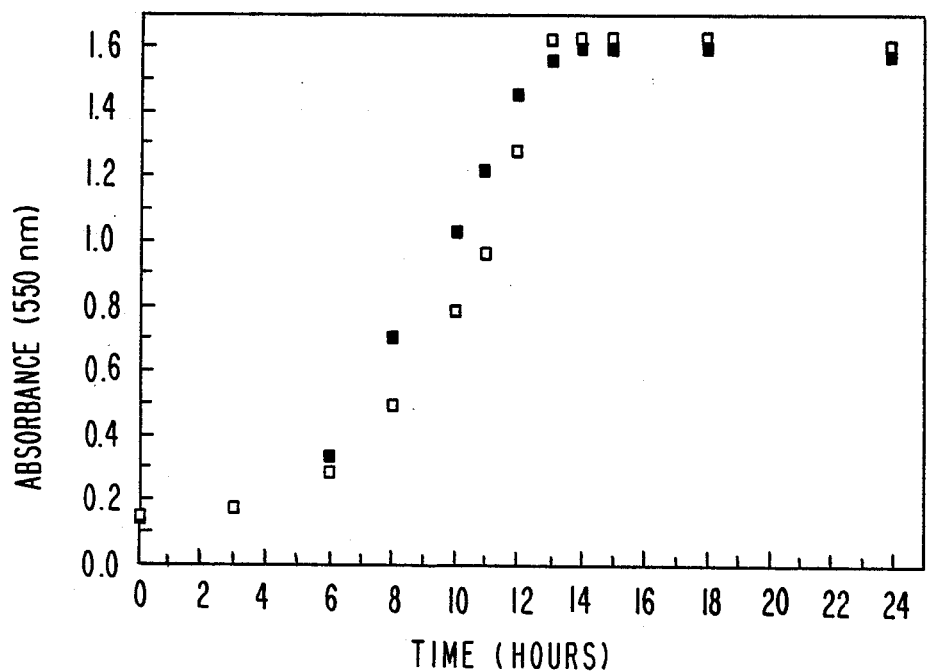
FIG. 6A shows growth curves for wild type and acetaldehyde tolerant strains of *Z. mobilis* at 0.0% (w/w) acetaldehyde. Symbols: ■ wild type; ☐ strain AT1.0 Screw cap test tube culture, 4GSM.
Figure 6B:
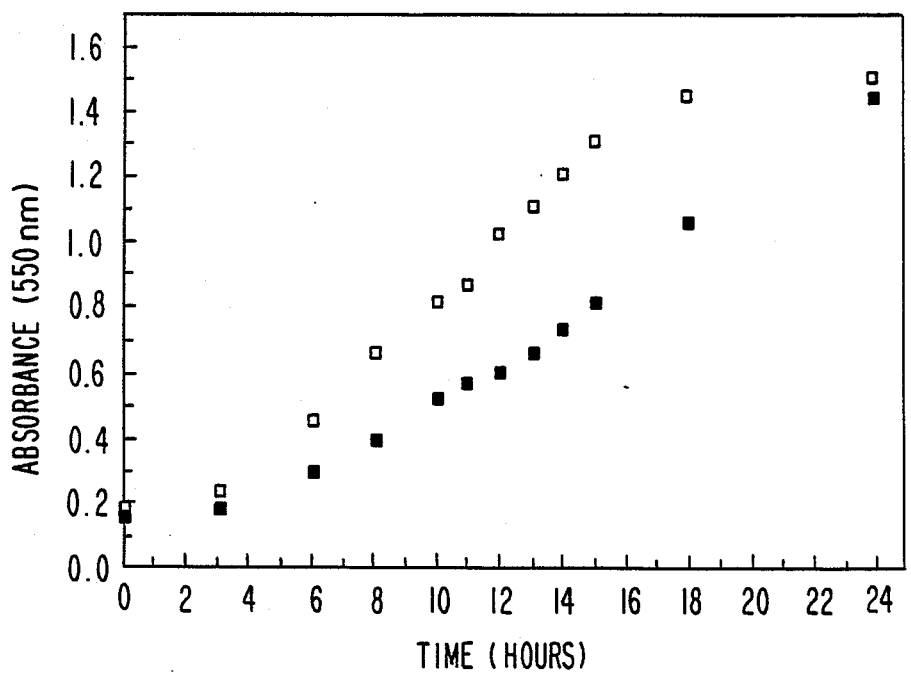
FIG. 6B shows growth curves for wild type and acetaldehyde tolerant strains of *Z. mobilis* at 0.1% (w/w) acetaldehyde. Symbols: ■ wild type; ☐ strain AT1.0. Screw cap test tube culture, 4GSM.
Figure 6C:
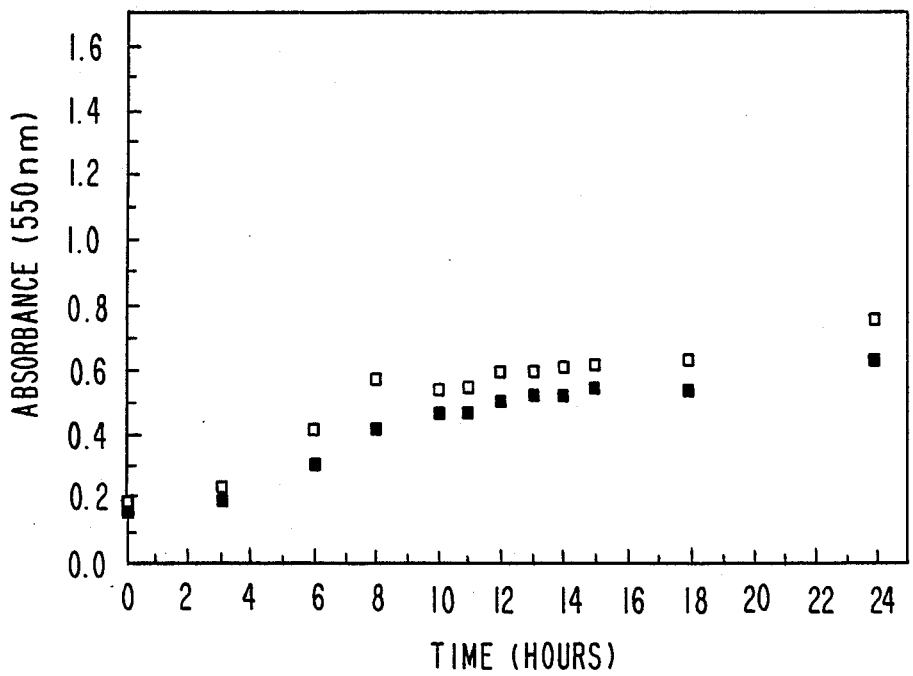
FIG. 6C shows growth curves for wild type and acetaldehyde tolerant strains of *Z. mobilis* at 0.2% (w/w) acetaldehyde. Symbols: ■ wild type; ☐ strain AT1.0. Screw cap test tube culture, 4GSM.

The growth rate of *Z. mobilis* was inhibited by as little as 0.01 to 0.05% (wt/wt) added acetaldehyde (see FIG. 5). FIGS. 6A, 6B, and 6C show growth curves for both the wild type *Z. mobilis* and for the strain AT1.0 which had been selected for tolerance to acetaldehyde in a 1.0% acetaldehyde chamber. When grown at 0.0% (wt/wt) added acetaldehyde the tolerant strain showed a growth curve similar to that of the wild type (FIG. 6A). At 0.1% added acetaldehyde, however, the selected strain showed a higher rate of growth than that of the wild type (FIG. 6B). This tolerance was also seen at 0.2% added acetaldehyde, although the growth rate of both strains sharply decreased in this environment (FIG. 6C). When both the wild type and AT1.0 strains were cultured in screw cap tubes with 0.1% added acetaldehyde, there was a decrease in the level of acetaldehyde in solution. A slightly larger drop in acetaldehyde was associated with the growth of the tolerant strain (see Table 3).

TABLE 3

Decreases in acetaldehyde level upon culturing. Screw cap test tube culture, 24 hours.

| Culture | Final % (w/w) acetaldehyde |
|---|---|
| Sterile | 0.11 |
| Wild type | 0.04 |
| AT1.0 | 0.03 |

In addition, when allyl alcohol mutant 17-50x was further selected in a 1.6% acetaldehyde chamber, the resultant strain 17-50x1.6 produced approximately 53% less acetaldehyde than strain 17-50x and 16% less acetaldehyde than the wild type during shake flask culture (see Table 4).

TABLE 4

Acetaldehyde production by wild type, allyl alcohol selected, and allyl alcohol/acetaldehyde tolerant selected strains. 4GSM shake flask culture, 24 hours

| Culture | % (w/w) acetaldehyde |
|---|---|
| Wild type | 0.078 |
| 17-50x | 0.139 |
| 17-50x16 | 0.066 |

DISCUSSION

The range of acetaldehyde production by *Z. mobilis* strains selected using 0.2 mM allyl alcohol is similar to that reported by Wills et al, *supra*. The acid fuchsin overlay technique proved to be useful for the differentiation of acetaldlehyde production by those strains selected using allyl alcohol. The diffusion of the acetaldehyde, however, limited the resolution of the overlay to about 30 colonies per plate. Therefore, the overlay technique was impractical for use with a mutagen alone. The range of mutants was thereby limited to those acquired by allyl alcohol selection. This is a disadvantage since two allyl alcohol selected mutants have been shown to have a single amino acid substitutions [Wills et al (1979) *Eur. J. Biochem.* 99:323–331] and as such would be more likely to revert than deletion mutants.

The decrease in the combined yield of ethanol and acetaldehyde for strains selected at increased levels of allyl alcohol was potentially due to a slower growth rate for the allyl alcohol selected strains, to an increase inside reaction product formation, or to both factors. A decrease in growth rate was noted for strain 17-500x when grown under shake flask conditions. No difference, however, was noted between the growth rates of the wild type and 17-500x strains during screw cap tube culture. Since the growth rate of the wild type was shown to be inhibited by between 0.0 and 0.05% (wt/wt) added acetaldehyde, the difference in growth rate between the two strains during shake flask culture may be related to differences in the level of acetaldehyde production by the two strains when grown under increased oxygen tension. No difference in final pH was observed between the wild type and 17-500x strains grown in shake flask culture. This suggests that little to no excess acetic acid or lactic acid was produced in response to the decrease in alcohol dehydrogenase activity. Tests have not yet been conducted to determine whether there was any increase in sorbitol production by strain 17-500x over that of the wild type. Sorbitol is produced by *Z. mobilis* [Barrow et al (1984) *Appl. Microbiol. Biotechnol.* 20:225–232; Viikari (1984) *Appl. Microbiol. Biotechnol.* 20:118–123]; the greater reducing power of the increased NADH levels within the cell might produce polyhydroxylated compounds such as sorbitol or glycerol.

Approximately twice as much acetaldehyde was recovered by culturing strain 17-500x under batch stripped-acetaldehyde respiration as opposed to culturing under shake flask conditions. This increase in the level of acetaldehyde produced may be attributed to: the decreased inhibition of growth due to separation of the acetaldehyde from solution, the loss of acetaldehyde from the nonaerated shake flasks due to volatility of the acetaldehyde, and, the limitation of alcohol dehydrogenase activity due to the increased level of oxygen available to the cells. Previous work has indicated that *Z. mobilis* does not show an increase in growth yield in the presence of oxygen; this may be the result of the formation of toxic products, specifically, acetaldehyde [Bringer et al (1984) *Arch. Microbiol.* 139:376–381].

In this study, 4.08 g/l of acetaldehyde was produced from 4.0% (wt/wt) glucose when strain 17-500x was grown under batch stripped-acetaldehyde respiration. This level of acetaldehyde production compares favorably to the accumulation of 1.3 g/l acetaldehyde in an aerated continuous culture of wild type *Z. mobilis* with a feed stream of 14% glucose as reported by Bringer et al, suora. In addition, the level of acetaldehyde production achieved in this study is competitive with the 3.5 g/l acetaldehyde formed from the oxidation of 65 g/l ethanol by whole cells of *Candida utilis* [Armstrong et al (1984) *Biotechnol. Lett.* 6:183–188].

The growth rate of *Z. mobilis* is greatly decreased in the presence of acetaldehyde. In addition, the efficiency of stripping acetaldehyde from solution decreases with the decreasing concentration of acetaldehyde in solution. Therefore, the selection of acetaldehyde tolerant mutants is of critical concern to the overall feasibility of stripped-acetaldehyde respiration. It is not clear which change in genotype might be responsible for the increase in tolerance to acetaldehyde. Since Z. mobilis does not appear to have an aldehyde dehydrogenase to convert acetaldehyde to acetate, the decrease in acetaldehyde may instead be due to the formation of complexes between acetaldehyde and protein or other cellular material. The acetaldehyde tolerant strains have a more translucent milky appearance in colony morphology, although no difference in cellular morphology could be ascertained microscopically at 1000x magnification. Although the data obtained indicate that it is possible to select for Z. mobilis tolerant to acetaldehyde, it is important to determine whether this phenotype can be compatible with increased acetaldehyde production by the organism.

Figure 7:
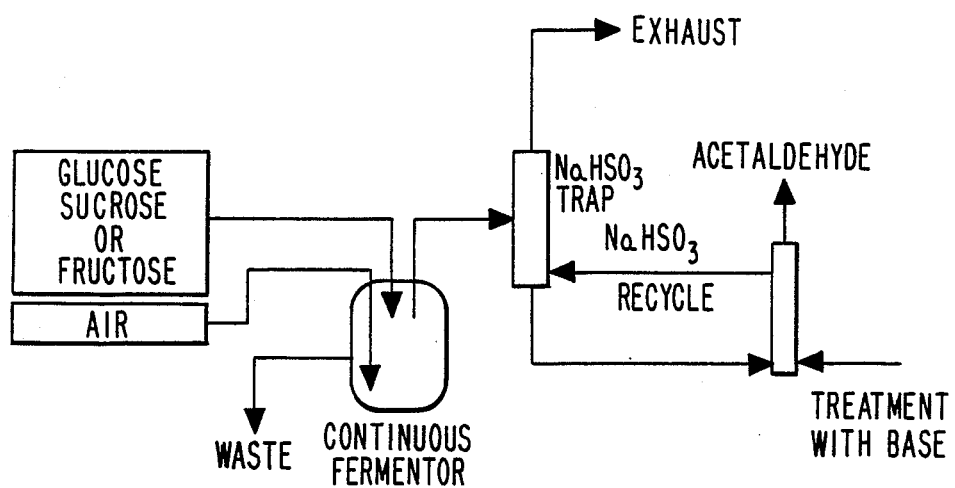
FIG. 7 shows a preferred scheme for the production of acetaldehyde using continuous stripped-aetaldehyde respiration.

Stripping acetaldehyde from the growing culture is advantageous in that it decreases growth inhibition due to product buildup and represents a potentially economical means of product recovery. If the acetaldehyde is efficiently recovered from the exhaust gases, the stripped-acetaldehyde respiration represents an important advantage over the fermentation of ethanol; the product is continuously separated from solution without the need for a distinct distillation step. Thus, it might be feasible to use stripped-acetaldhyde respiration in a continuous system such as is shown in FIG. 7. To increase the efficiency of acetaldehyde production and to further understand the commercial feasibility of this product method, a number of factors must be addressed: the techniques for the selection of mutants with increased tolerance to acetaldehyde and increased levels of acetaldehyde production, the stabilization of the selected mutants, the optimization of oxygen delivery rate and efficiency of gas stripping, and, the method of trapping acetaldehyde from the exhaust gases.

It is noted that the above Z. mobilis strain 17-500x (also known as RZIE (10998)) has been deposited with the ATCC under the Budepest Convention for patent purposes with accession No. ATCC 53717.

What is claimed:

1. A method of obtaining an acetaldehyde producing strain of Z. mobilis which comprises (a) selecting a strain having decreased alcohol dehydrogenase activity by growing a first strain of Z. mobilis in the presence of consecutively higher concentrations of allyl alcohol sufficient to kill a majority of the starting number of cells and selecting an acetaldehyde producing strain from the remaining viable microorganisms and further processing the resulting acetaldehyde producing Zymomonas mobilis strain to select an aldehyde tolerant mutant by chemical mutagenesis wherein said selection is effected in the presence of vapor phase acetaldehyde.

2. An improved acetaldehyde producing strain of Z. mobilis produced by
   a method which comprises (a) selecting a strain having decreased alcohol dehydrogenase activity by growing a first strain of Zymomonas mobilis in the presence of consecutively higher concentration of allyl alcohol sufficient to kill a majority of the starting number of cells and selecting an acetaldehyde producing strain from the remaining viable microorganisms; and
   (b) further processing the resulting acetaldehyde producing Zymomonas mobilis strain to select an aldehyde tolerant mutant by chemical mutagenesis wherein said selection is effected in the presence of vapor phase acetaldehyde.

3. An acetaldehyde producing strain of Z. mobilis as in claim 2 which is ATCC 53717.

4. A method of microbially producing acetaldehyde which comprises culturing an acetaldehyde producing strain of Z. mobilis, as in claim 2, in a carbohydrate containing medium under direct aeration to produce acetaldehyde, the rate of aeration being sufficient to substantially remove product acetaldehyde from the medium.

5. A method as in claim 4 wherein the product acetaldehyde is subsequently removed from the aeration exhaust gases by forming an acetaldehyde-bisulfite addition product.

* * * * *

UNITED STATES PATENT AND TRADEMARK OFFICE
CERTIFICATE OF CORRECTION

PATENT NO. : 4,900,670
DATED : Feb. 13, 1990
INVENTOR(S) : Zall et al

It is certified that error appears in the above-identified patent and that said Letters Patent is hereby corrected as shown below:

In the Title, change "Acetaldevae" to --Acetaldehyde--.

Column 2, line 3, change "ethyene" to --ethylene--.

Column 2, line 8, change "Zvmomonas" to --Zymomonas--.

Column 2, line 31, change "Zvmomonas" to --Zymomonas--.

Column 2, line 26, change "fermente" to --fermenter--.

Column 3, line 17, change "1 in 51 x $10^8$" to --1 in 1 x $10^8$--.

Column 4, line 56, delete "110".

Column 5, line 42, delete "25".

Column 6, line 15, change "$NaHS_3$" to --$NaHSO_3$--.

Column 8, line 49, change "17-50x" to --17-500x--.

Column 8, line 50, change "ties" to --times--.

Signed and Sealed this

Twenty-second Day of October, 1991

Attest:

HARRY F. MANBECK, JR.

*Attesting Officer*

*Commissioner of Patents and Trademarks*